(12) United States Patent
Gleditzsch et al.

(10) Patent No.: US 8,401,690 B2
(45) Date of Patent: Mar. 19, 2013

(54) METHOD FOR MACHINING A BLANK HAVING AN INDIVIDUAL SCALE-UP FACTOR AND BLANK THEREFOR

(75) Inventors: Siegfried Gleditzsch, Heppenheim (DE); Franz Basler, Laudenbach (DE); David Figge, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 215 days.

(21) Appl. No.: 12/896,395

(22) Filed: Oct. 1, 2010

(65) Prior Publication Data

US 2011/0115210 A1      May 19, 2011

Related U.S. Application Data

(63) Continuation of application No. PCT/EP2009/053999, filed on Apr. 3, 2009.

(30) Foreign Application Priority Data

Apr. 3, 2008    (DE) .................... 10 2008 017 473
Apr. 24, 2008   (DE) .................... 10 2008 020 720

(51) Int. Cl.
*G06F 19/00* (2011.01)

(52) U.S. Cl. ...................... 700/163; 433/201.1

(58) Field of Classification Search .................. 700/159, 700/163, 195; 433/201.1, 202.1; 428/542.8
See application file for complete search history.

(56) References Cited

U.S. PATENT DOCUMENTS

| | | |
|---|---|---|
| 3,665,493 A | 5/1972 | Glowzewski et al. |
| 4,615,678 A | 10/1986 | Moermann et al. |
| 4,988,297 A | 1/1991 | Lazzara et al. |
| 5,092,022 A | 3/1992 | Duret |
| 5,273,429 A | 12/1993 | Rekow et al. |
| 5,342,696 A | 8/1994 | Eidenbenz et al. |
| 5,359,511 A | 10/1994 | Schroeder et al. |
| 5,378,091 A | 1/1995 | Nakamura |
| 5,556,278 A | 9/1996 | Meitner |
| 5,716,215 A | 2/1998 | Blacklock |
| 5,788,494 A | 8/1998 | Phimmasone |

(Continued)

FOREIGN PATENT DOCUMENTS

| | | |
|---|---|---|
| AU | 762679 B2 | 7/2003 |
| DE | 196 12 699 C1 | 7/1997 |

(Continued)

OTHER PUBLICATIONS

English-language translation of the German Office Action—2 pages.

(Continued)

*Primary Examiner* — Ryan A. Jarrett
*Assistant Examiner* — Chad Rapp
(74) *Attorney, Agent, or Firm* — Fitzpatrick, Cella, Harper & Scinto

(57) ABSTRACT

In a method for processing a blank (1), in which the blank (1) can be densely sintered with shrinkage following machining and machining of the blank (1) is carried out in a machining device (7) allowing for an individual scale-up factor (F) relevant to the blank (1) for compensating for the shrinkage occurring during dense sintering, a linear measurement of the blank (1) is performed in one or more of the dimensions length, width, and height for determining the scale-up factor (F), wherein the measured linear measure (1) bears a known relationship to the scale-up factor (F), the type of blank (1) being known. Linear measurement of the blank (1) can be carried out in the machining device (7).

12 Claims, 2 Drawing Sheets

U.S. PATENT DOCUMENTS

| | | | |
|---|---|---|---|
| 5,846,079 | A | 12/1998 | Knode |
| 5,989,029 | A | 11/1999 | Osorio et al. |
| 6,126,445 | A | 10/2000 | Willoughby |
| 6,142,782 | A | 11/2000 | Lazarof |
| 6,224,371 | B1 | 5/2001 | De Luca |
| 6,231,342 | B1 | 5/2001 | Osorio et al. |
| 6,354,836 | B1 | 3/2002 | Panzera et al. |
| 6,394,880 | B1 | 5/2002 | Basler et al. |
| 6,398,554 | B1 | 6/2002 | Perot et al. |
| 6,482,284 | B1 | 11/2002 | Reidt et al. |
| 6,485,305 | B1 | 11/2002 | Pfeiffer |
| 6,640,150 | B1 | 10/2003 | Persson et al. |
| 6,666,684 | B1 | 12/2003 | Names |
| 6,968,247 | B2 | 11/2005 | Rathke et al. |
| 6,970,760 | B2 | 11/2005 | Wolf et al. |
| 7,086,863 | B2 | 8/2006 | Van der Zel |
| 7,226,338 | B2 | 6/2007 | Duncan et al. |
| 2002/0090592 | A1 | 7/2002 | Riley et al. |
| 2003/0073394 | A1 | 4/2003 | Reidt et al. |
| 2005/0254064 | A1* | 11/2005 | Basler .................. 356/601 |
| 2006/0106484 | A1 | 5/2006 | Saliger et al. |
| 2006/0141250 | A1 | 6/2006 | Basler et al. |
| 2006/0292527 | A1 | 12/2006 | Basler et al. |
| 2007/0050072 | A1 | 3/2007 | Schwotzer |
| 2009/0273108 | A1 | 11/2009 | Koebel et al. |

FOREIGN PATENT DOCUMENTS

| | | | |
|---|---|---|---|
| DE | 196 54 055 | A1 | 6/1998 |
| DE | 197 33 161 | A1 | 2/1999 |
| DE | 103 30 758 | A1 | 2/2005 |
| DE | 10 2004 063 417 | A1 | 7/2006 |
| DE | 10 2006 052 027 | A1 | 5/2008 |
| DE | 102006052027 | A1 | 5/2008 |
| EP | 0 160 797 | A1 | 11/1985 |
| EP | 0 455 854 | A1 | 11/1991 |
| EP | 0 850 601 | A2 | 7/1998 |
| EP | 0 904 743 | A2 | 3/1999 |
| EP | 1 023 876 | A2 | 8/2000 |
| EP | 1 062 916 | A2 | 12/2000 |
| EP | 1 252 867 | A1 | 10/2002 |
| EP | 1 067 880 | B1 | 10/2003 |
| EP | 1 658 825 | A1 | 5/2006 |
| JP | 10 277059 | A | 10/1998 |
| WO | 99/13796 | A1 | 3/1999 |
| WO | 99/47065 | A1 | 9/1999 |
| WO | 0135854 | A1 | 5/2001 |
| WO | 03/007834 | A1 | 1/2003 |
| WO | 03024352 | A1 | 3/2003 |
| WO | 2004060197 | A1 | 7/2004 |
| WO | 2005002463 | A1 | 1/2005 |

OTHER PUBLICATIONS

English-language translation of the Written Opinion of the International Searching Authority—3 pages.

Kucey et al., "The Procera Abutment—The Fifth Generation Abutment for Dental Implants," Journal of Canadian Dental Association, vol. 66, No. 8 (2000) 445-49.

European Patent Office, "Internationaler Vorlaufiger Bericht Uber Die Patentierbarkeit" issued in International Application No. PCT/EP2008/060043, 6 pages, Oct. 19, 2009 (and English translation thereof).

European Patent Office, "Schriftlicher Bescheid Der Internationalen Recherchenbehorde" in connection with International Application No. PCT/EP2009/053999, 6 pages, Oct. 3, 2010 (and English translation thereof).

At least partial English translation of Office Action issued Feb. 12, 2009, by the German Patent Office in connection with International Application No. PCT/EP2009/053999, 2 pages.

* cited by examiner

METHOD FOR MACHINING A BLANK HAVING AN INDIVIDUAL SCALE-UP FACTOR AND BLANK THEREFOR

CROSS REFERENCE TO RELATED APPLICATIONS

This application is a continuation of International Application No. PCT/EP2009/053999, filed Apr. 3, 2009, and claims priority to German Patent Application Nos. 10 2008 017 473.4, filed Apr. 3, 2008, and 10 2008 020 720.9, filed Apr. 24, 2008, each of which is incorporated by reference herein in its entirety, as if set forth fully herein.

TECHNICAL FIELD

The invention relates to a method for machining a blank, allowing for an individual scale-up factor, and a blank therefor.

PRIOR ART

Dental restorations made of zirconium oxide and aluminum oxide are initially produced in an overlarge form from a merely presintered blank and are then densely sintered in a high-temperature furnace with shrinkage. For every batch comprising a plurality of blanks, the scale-up factor required for production in an overlarge form is determined from the shrinkage, that is, from the linear change occurring during dense sintering. The term scale-up factor is understood to mean the ratio of $l_0/l$, where $l_0$ is the initial dimension prior to dense sintering and $l$ is the final dimension following dense sintering.

A sinter shrinkage parameter corresponding to the degree of shrinkage can alternatively be determined instead of the scale-up factor. These quantities are interchangeable for the person skilled in the art.

The accuracy of the scale-up factor or degree of shrinkage substantially determines the fitting accuracy of a finished prosthetic item when subsequently inserted into the patient's mouth. Differences in the density and thus in the degree of shrinkage within a batch, for which one and the same scale-up factor is specified, are a decisive factor influencing the inaccuracy of the scale-up factor and thus of the resulting fit of the restoration.

These differences in density or shrinkage within a batch are substantially caused by variations in the production steps of compression and presintering. By using smaller batch sizes during presintering, the accuracy of the scale-up factor can albeit be improved for all blanks in a batch, but the expense is considerable.

It is known from EP 1 067 880 B1 to apply an information code to a blank made of a porous ceramics material, which information code can be detected mechanically or by means of human sensory organs and which contains data concerning the individual input required to yield a compensatory scale-up factor. The identification code can be applied so as to be detectable optically, electromagnetically, or mechanically by tactile means. The scale-up factor results from the density of the prefabricated blank and the achievable density following the sintering process. An overlarge framework is machined by the removal of material from the blank made of a porous ceramics material, and the finished overlarge framework is densely sintered. During the sintering process, the framework shrinks linearly according to the individual scale-up factor without further deformation or distortion.

A blank for producing dental shaped bodies is disclosed in EP 0 160 797 A1, which blank comprises a blank corpus to be machined and a holder for the same. Reference surfaces containing coded information that can be scanned by the machining device and that relate to the properties of the blank are provided on the holder. This information is queried by a touch probing operation carried out by the machining tool on the reference surface.

By means of an individual scale-up factor disclosed in EP 1 067 880 B2, an improvement can be achieved in the quality of the fit of dental restorations since an individual scale-up factor is assigned to each blank.

It is an object of the invention to provide an improvement in the fitting accuracy of dental restorations by allowing for an individual scale-up factor for each blank when machining each blank of a batch produced by means of a presintering process, so as to carve a dental restoration from said blank.

SUMMARY OF THE INVENTION

The method of the invention and a blank formed for carrying out this method improve the fitting accuracy of dental restorations to be produced therewith. The blanks are also referred to as blocks, and they represent shaped bodies each having dimensions that are characteristic of a group of blanks, and the blanks as such can have an arbitrary geometry. That is to say, not only cuboid blocks but also cylindrical blocks and blocks of other shapes are suitable.

The invention thus relates to a method for machining a blank, the blank being densely sintered with shrinkage following machining. The blank is machined in a machining device to a degree allowing for a scale-up factor for compensating for the shrinkage occurring in subsequent dense sintering. The term "scale-up factor" is understood to mean an individual scale-up factor related to a specific blank of a production batch. For the purpose of determining the scale-up factor, a linear measurement of the blank is carried out in one or more dimensions of length, width, and height.

The measured linear measure bears a previously known relationship to the scale-up factor for a known type of blank.

In industrial ceramics, it has been practice known for many years to determine the scale-up factor by means of a linear measurement of the blank to determine the individual volume of the blank. However, it is an expensive procedure to determine the scale-up factor by means of a plurality of linear measurements for every blank of the batch and to apply the individual scale-up factor to the blank.

The invention is based on the assumption that the type of blank and the expected properties assigned to this type of blank are known at the time of linear measurement and that there exists a correlation between the linear measure and the scale-up factor, which correlation is dependent on this blank type and is used for machining the blank to an over-large shape.

For example, the linear measure obtained following dense sintering of a blank from this batch can be referred to as the expected characteristic in this case, from which linear measure, for example, a scale-up factor can then be calculated directly or taken from a table. This expected characteristic can be notified on the blank itself or in the accompanying documents in the form of batch-related information and must then be transmitted to the machining device before the machining process takes place.

The linear measurement of the blank can be carried out externally or in the machining device or as a combination of an external measurement and a measurement taken inside the machining device. If the linear measurement is carried out externally of the machining device, the measuring device, for example, a mechanical or optical measuring device, can be connected to the machining device and it can transmit the measured value directly to the machining device, or the machining device can comprise input means for the linear measure for inputting said linear measure into the same manually.

Preferably, the linear measurement of the blank can be carried out in the machining device, for example, by means of a touch probing operation performed by a tool on the blank. It is not strictly necessary in this case to provide a scanner in the machining device for detecting a bar code. The linear measurement can alternatively be carried out as a non-contact measurement, for example, by optical measurement.

The advantage of determining the individual scale-up factor in the machining device according to the invention is that the scale-up factor or the degree of shrinkage can be determined for every blank of the batch without requiring an additional production step to be carried out by the manufacturer.

The further advantage of determining the individual scale-up factor in the machining device is that accidental confusion following the insertion of the blank into the machining device can be obviated.

According to the invention, the blank can be presintered or even merely compressed, that is, without presintering, and it can be made of a ceramic or metallic material.

The measurement of a plurality of dimensions results in a separate scale-up factor for every dimension measured.

Advantageously, the linear measurement can be carried out on one, two, or all three dimensions.

In an advantageous development, at least two or all three of the dimensions of the blank are measured for the purpose of determining the scale-up factor with greater accuracy.

The accuracy of the scale-up factor can be increased by averaging a large number of measured values obtained from a plurality of measurements.

It is important, particularly in the case of anisotropically shrinking blanks, to allow for the shrinkage of the blank separately for each spatial direction.

Particularly in the case of anisotropic materials, the accuracy of the scale-up factor can be increased when the individual scale-up factor is determined separately for each dimension and is allowed for in the calculation carried out separately for each dimension of the item to be produced in an overlarge form by machining the workpiece.

If a correction of the scale-up factor for the individual spatial directions is necessary, it can be effected by way of predetermined correction values.

Even when the blank has no exact standard dimensions, e.g. when it is slightly bent, a scale-up factor can be determined from measurement in the other dimensions.

In an advantageous development, for determining the linear measure in a first dimension, a plurality of linear measurements are carried out at a distance from each other in at least one other dimension, and a linear measure for the dimension in the first direction is determined from said plurality of linear measurements. It is thus possible to compensate for differences in the first dimension.

For determining the scale-up factor, when a first linear measure is determined in a first dimension y and this first linear measure is located outside a tolerance range, at least one linear measurement can be carried out in at least one other dimension x, z, and a scale-up factor determined.

It will thus be possible to machine even non-ideal blanks as workpieces.

Advantageously, correction factors for differences in the scale-up factor in the individual spatial directions x, y, z can be applied to the workpiece such that these correction factors can be detected and allowed for when determining the scale-up factor.

A further object of the invention is a blank made of a material to be compacted with shrinkage by means of a sintering process. This blank comprises an information code comprising batch-related data and correction parameters for the shrinkage in the individual spatial directions x, y, z.

A blank of such type enables batch-related anisotropies of the material to be allowed for with justifiable effort in the production of the overlarge component by carving material from the blank and thus provides an improvement in the accuracy of the scale-up factor.

Advantageously, the weight of the blank or the blank corpus forming part of the blank can be included in the information code. Furthermore, other batch-related values such as the compression parameters or the presintering parameters can be included in the information code.

BRIEF DESCRIPTION OF THE DRAWINGS

An exemplary embodiment of the invention is illustrated in the drawings, in which.

EXEMPLARY EMBODIMENTS

Figure 1:
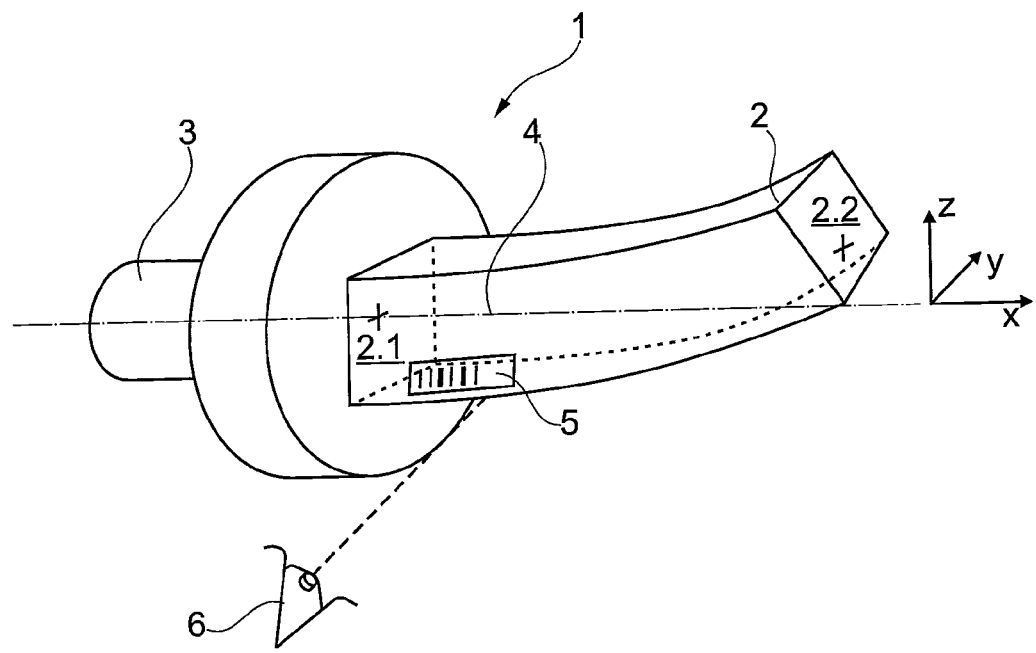
FIG. 1 shows a workpiece in the form of a blank comprising a blank corpus and a holder.

A workpiece for producing a dental restoration item is shown in FIG. 1. The workpiece is a blank 1 comprising a blank corpus 2 and a holder 3 attached thereto for mounting the blank in a machining device (not shown).

Suitable materials for the workpieces are ceramic or metallic materials, whilst the workpieces can be partially sintered blanks and merely compressed blanks, also referred to as green compacts. After CAM machining, the workpieces are densely sintered with shrinkage for the purpose of producing a desired item. The presintered blank can be machined with removal of material, for example, by means of a milling or grinding process.

The blank corpus 2 shown is presintered and is shown as being twisted about a center axis 4 and also bent about the center axis, thus deviating from an ideal shape as a result of presintering.

An information code in the form of a bar code 5 that can be read, for example, by a scanner 6 outside or inside a machining device is applied to the blank corpus 2.

This code can contain correction factors applied to the blank for differences in the scale-up factor in the different spatial directions x, y, z, which correction factors are to be allowed for when determining the scale-up factor. These correction factors can be batch-dependent or they can be specific to the material used.

Figure 2:
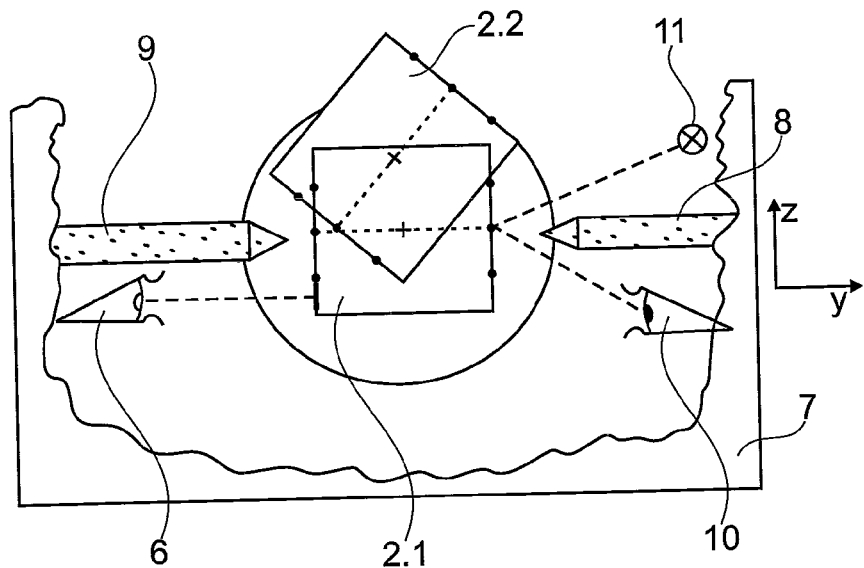
FIG. 2 is a top view of the workpiece shown in FIG. 1 that has been inserted into a machining device comprising two machining tools.

FIG. 2 is a top view of the workpiece 2 shown in FIG. 1 in a machining device 7 comprising two machining tools 8, 9, the deviation from the ideal state being indicated by the two front surfaces 2.1, 2.2 of the blank corpus 2. The lateral surfaces of the blank corpus 2 are omitted for the sake of clarity.

The position of the blank corpus is detected by two machining tools 8, 9 adapted to carry out touch probing operations on the blank corpus 2. This makes it possible to achieve a linear measurement in a spatial direction y. If only one machining tool 8 or 9 were used, the blank would have to be rotated through 180°, in order to determine the linear measure from two measurements and the known distance from the rotation axis of the blank.

Instead of a tool carrying out a touch probing operation, the position of the blank corpus can alternatively be measured by means of a non-contact scanning device in the form of optical scanning by means of a sensor 10 and a point light source 11, as shown in FIG. 2.

In order to compensate for inaccuracies occurring due to misalignment, it is possible to carry out a plurality of touch probing operations at a plurality of positions deviating from each other in the x or z direction, as illustrated by the circles. By averaging the values obtained from repeated measurements in the same dimension y, an average value for the linear measure $l_0$ can be obtained, from which the scale-up factor can be derived.

Figure 3:
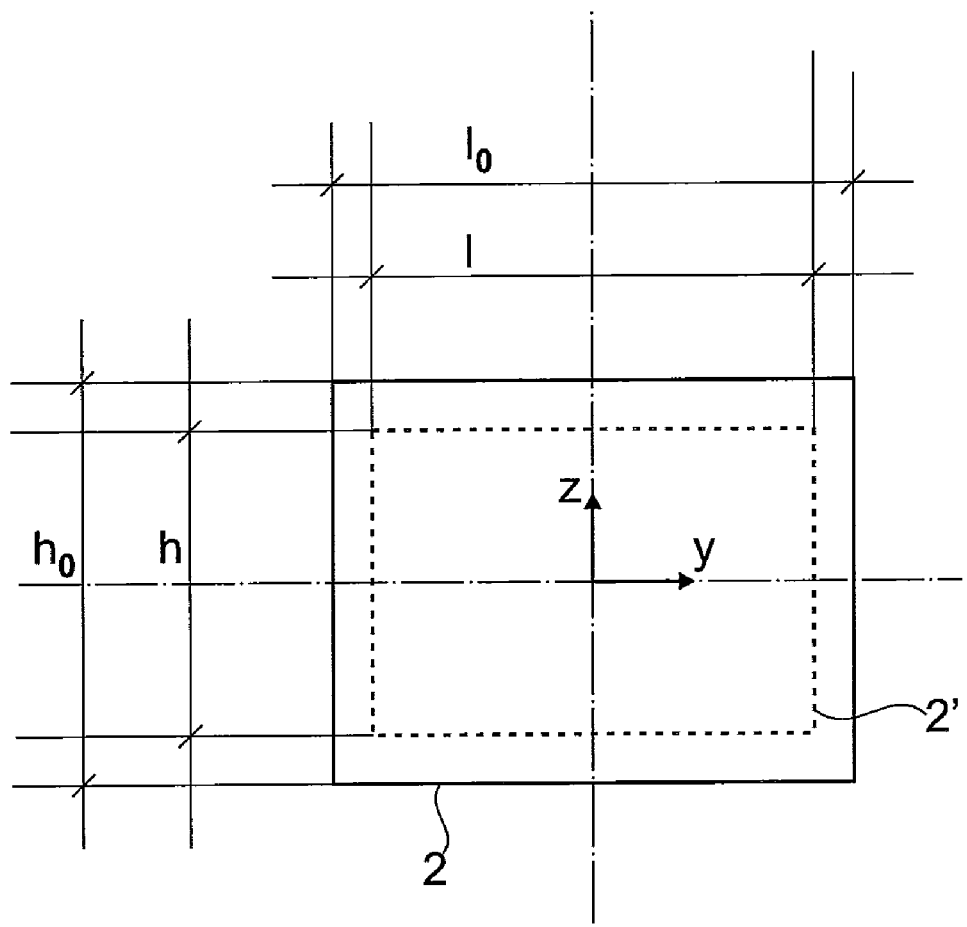
FIG. 3 shows a front surface of the blank shown in FIG. 1.

FIG. 3 illustrates the possibility of allowing for different scale-up factors in different spatial directions z, y in the case of anisotropic shrinkage of the blank 2 during the sintering process. The possibly different scale-up factors for the three directions in space can be determined by means of a measurement carried out for each of the three directions. The linear measures $l_0$ and $h_0$ of the blank 2 in the y-z plane and the linear measures l and h of the densely sintered blank 2' are shown in the present case.

In the case of anisotropic shrinkage, it is possible for the differences in the scale-up factor in the directions in space to be determined in advance outside the machine as a batch-dependent value or as a theoretical material value per se.

This is not necessary in the case of isotropic shrinkage. On the contrary, it is sufficient for the determination to be carried out in only one dimension or for all three dimensions to be processed to form an scale-up factor F, the accuracy of the scale-up factor F being improved by the greater number of measured values.

The individual scale-up factor F can be determined by comparing the measured linear measure $l_0$ with a linear measure l specified for this workpiece and to be expected following dense sintering of the workpiece. This expected linear measure l is shown in the present case in the spatial direction y.

Starting from a known type of blank 2 having a known characteristic linear measure l, the measured linear measure $l_0$ can directly lead to the scale-up factor F on the assumption that the shrinkage is linear.

This dimension l that is characteristic of the blank can be stored, possibly together with other properties of the blank, in the control software of the machining device, and, before the workpiece is machined in the machining device, the scale-up factor F is determined by the machining device using the measured linear measure $l_0$.

In the case of a change in length, the equation $F=l_0/l$ yields the scale-up factor F, where $l_0$ is the initial length before the sintering process and l is the length following sintering.

The formula $S=(l_0-l)/l$ yields the degree of shrinkage. Usually, the shrinkage due to sintering is processed in the form of a scale-up factor F by the software of the machining device.

For example, when the final dimension l is 10 mm and a linear measure $l_0$ is 12 mm, the scale-up factor F can be directly determined as being 1.2. The degree of shrinkage is in this case 0.2 or 20%.

Additionally or alternatively, the correlation that is characteristic of the workpiece between the measured linear measure $l_0$ and the scale-up factor F can be stored in the software, for example, in the form of a function or a table.

The calculation of the scale-up factor Fx,y,z in the form of an scale-up factor for the spatial directions x, y, and z is based on the equation $F=l_0/l$, where $l_0$ is a length that is measured in the machining device in any of the spatial directions prior to dense sintering. l is the expected theoretical length following dense sintering and is taken, for example, from a database for the respective type of blank.

In general, the scale-up factor can be determined from the mass m of the respective type of blank and from a determined density Ds of the densely sintered ceramics material. This means that in the case of a constant block mass m of a known given block size, the degree of shrinkage of the workpiece or the item produced therefrom can be computed from a measured length $l_0$ and, if appropriate, from more than one length.

Alternatively, the scale-up factor F can be determined from a pre-known correlation $F=f(l_0)$ between the scale-up factor F and the measured length $l_0$, for example, according to the formula $Fx,y,z=a*l_0+b$, where the parameters a, b are known from a predetermined correlation for the respective type of blank.

In this case, there exists a known correlation between the linear measure $l_0$ and the scale-up factor F for every type of block. This correlation depends significantly on the combined compressing and presintering processes of the blanks prior to being machined in the machining device.

In the exemplary embodiment I, the scale-up factor is determined from Ds and m and three factors. A block having the dimensions length $l_0$, width $b_0$, and height $h_0$ is used as the blank. The length $l_0$ of the blank is determined by a touch probing operation in the machining device. The mass m of the blank is known in advance for the entire batch and is constant. The density $D_s$ of the blank following dense sintering is likewise known for the material used and for the type of blank and is constant The length l of a cubic blank following dense sintering can be calculated as follows, where m denotes the block mass and V the block volume following dense sintering:

$$D_s=m/V=m/l^3$$

$$l^3=m/D_s$$

$$l=(m/D_s)^{1/3}$$

The scale-up factor F for the dimension length can be calculated by using the formula $F=l_0/l$ on the measured length $l_0$ of the blank and the calculated length l following dense sintering. The scale-up factors for the dimensions width and height are determined similarly.

The scale-up factors for the three dimensions are then used by the machining software for the production of the desired item in overlarge form.

In the exemplary embodiment II, the scale-up factor F is determined from a correlation of the initial dimensions in the form of $F=f(l_0,b_0,h_0)$. This correlation between the scale-up factor and the linear measures length, width, and height is known in advance for the material used and for the type of blank. A blank such as the one used in Example I is employed. Likewise, any of the dimensions length, width, and height is determined in a touch probing operation as described in Example I.

The correlation is stored in the form of a mathematical function or as a data table in a software program and can be used for every single blank to determine the scale-up factor from the measured size of the blank and said correlation of the scale-up factor and the respective dimension or, in the case of linear shrinkage, starting from one dimension as representative of all dimensions. In the Exemplary Embodiment III, the scale-up factor is determined in all dimensions. A blank illustrated in Example I or Example II is used. For the purpose of increasing the accuracy of the scale-up factor, a scale-up factor for all three dimensions is determined by touch probing operations carried out in all three dimensions, that is, for length $l_0$, width $b_0$, and height $h_0$. The larger amount of measuring data thus involved increases the accuracy of the scale-up factor.

When anisotropic shrinkage is involved, the differences in shrinkage in the individual spatial directions are determined in advance in the form of batch-related values and stored in a bar code on the blank. Other batch-related characteristics can also be stored here.

In the exemplary embodiment IV, the scale-up factor is determined for a blank as shown in FIG. 1 that is bent, for example, distorted in length. As a result of presintering, the blank used exhibits a deviation from the ideal shape in the dimension x for linear measurement of the length. Another scale-up factor can then be determined from the linear measurements carried out in examples I to III and taken from a linear measure of a different dimension y, z, for example, the width and/or height. In particular, the use of batch-related information concerning deviations from isotropic shrinkage can improve the accuracy of the scale-up factor.

Averaging of the scale-up factors acquired from the linear measures obtained in one or more of the other dimensions y, z can produce a usable scale-up factor for the dimension x, in which the linear measure would have itself been unusable.

What we claim is:

1. A method for machining a blank, wherein said blank can be densely sintered with shrinkage following machining and machining of said blank is carried out in a machining device while allowing for an individual scale-up factor (F) relevant to said blank for compensation of the shrinkage occurring when dense sintering is carried out, the method comprising:
performing a linear measurement on said blank in one or more, others of dimensions of length, width, and height; and
determining an individual scale-up factor (F) from a measurement measured in the linear measurement and a pre-known relationship between the linear measurement and the scale-up factor (F), a type of the blank being known, wherein the linear measurement of the blank is performed in the machining device by a touch probing operation on the blank by means of a tool or by contactless scanning,
wherein the performing of the linear measurement includes performing a plurality of linear measurements at a distance from each other with reference to at least one of the other dimensions, and
wherein the performing of the linear measurement in the one of the dimensions is based on the plurality of linear measurements.

2. The method according to claim 1, wherein the pre-known relationship between the linear measurement and the scale-up factor relates to a specific type of the blank, and the determining of the individual scale-up factor is computed directly.

3. The method according to claim 1, wherein the pre-known relationship between the linear measurement and the scale-up factor relates to a specific type of the blank and the determining of the individual scale-up factor includes deriving the individual scale-up factor from a table.

4. The method according to any one of claims 1 to 3, wherein the blank has been presintered or merely compressed and consists of a ceramic or metallic material.

5. The method according to any one of claims 1 to 3, wherein the performing of the linear measurement is carried out for one, two, or all three dimensions (x, y, and z).

6. The method according to any one of claims 1 to 3, wherein the determining of the individual scale-up factor also includes taking average values over the three dimensions (x, y, and z).

7. The method according to any one of claims 1 to 3, further comprising performing a correction of the scale-up factor for individual dimensions (x, y, and z) via a previously ascertained anisotropy of a degree of shrinkage.

8. The method according to any one of claims 1 to 3, wherein the determining of the individual scale-up factor is performed by separately determining a scale-up factor for each dimension (x, y, and z), each scale-up factor being taken into account when determining, separately for each dimension (x, y, and z), dimensions of an overlarge item to be produced by machining the blank.

9. A method for machining a blank, wherein said blank can be densely sintered with shrinkage following machining and machining of said blank is carried out in a machining device while allowing for an individual scale-up factor (F) relevant to said blank for compensation of the shrinkage occurring when dense sintering is carried out, the method comprising:
performing a linear measurement on said blank in one or more of dimensions of length, width, and height; and
determining an individual scale-up factor (F) from a measurement measured in the linear measurement and a pre-known relationship between the linear measurement and the scale-up factor (F), a type of the blank being known, wherein the linear measurement of the blank is performed in the machining device by a touch probing operation on the blank by means of a tool or by contactless scanning,
wherein the performing of the linear measurement includes performing a first linear measurement in a first one of the dimensions, and performing at least one other linear measurement in at least one other of the dimensions when the first linear measurement is outside a tolerance range.

10. A method for machining a blank, wherein said blank can be densely sintered with shrinkage following machining and machining of said blank is carried out in a machining device while allowing for an individual scale-up factor (F) relevant to said blank for compensation of the shrinkage occurring when dense sintering is carried out, the method comprising:
performing a linear measurement on said blank in one or more of dimensions of length, width, and height; and
determining an individual scale-up factor (F) from a measurement measured in the linear measurement and a pre-known relationship between the linear measurement and the scale-up factor (F), a type of the blank being known, wherein the linear measurement of the blank is performed in the machining device by a touch probing operation on the blank by means of a tool or by contactless scanning,
wherein batch-related correction factors for differences in the scale-up factor in the individual dimensions are detectably provided on the blank and are accounted for when determining scale-up factors in the dimensions.

11. A method for machining a blank, wherein said blank can be densely sintered with shrinkage following machining and machining of said blank is carried out in a machining device while allowing for an individual scale-up factor (F)

relevant to said blank for compensation of the shrinkage occurring when dense sintering is carried out, the method comprising:

performing a linear measurement of said blank in one or more, others of dimensions of length, width, and height; and determining an individual scale-up factor (F) from a measurement measured in the linear measurement and a pre-known relationship between the linear measurement and the scale-up factor (F), a type of the blank being known, wherein the linear measurement of the blank is performed in the machining device by a touch probing operation on the blank by means of a tool.

12. A method for machining a blank, wherein said blank can be densely sintered with shrinkage following machining and machining of said blank is carried out in a machining device while allowing for an individual scale-up factor (F) relevant to said blank for compensation of the shrinkage occurring when dense sintering is carried out, the method comprising:

performing at least one linear measurement on said blank in at least one dimension, prior to dense sintering of said blank but after pre-sintering of said blank; and determining an individual scale-up factor (F) by performing a calculation that is a function of the at least one linear measurement and an expected linear measurement following the dense sintering, a type of the blank being known, wherein the at least one linear measurement is performed in the machining device by one of a touch probing operation on the blank by means of a tool or by contactless scanning.

\* \* \* \* \*